US008036913B1

(12) United States Patent
Pinsonneault et al.

(10) Patent No.: US 8,036,913 B1
(45) Date of Patent: Oct. 11, 2011

(54) SYSTEMS AND METHODS FOR PRESCRIPTION PRE-FILL PROCESSING SERVICES

(75) Inventors: Roger Pinsonneault, Alpharetta, GA (US); Scott MacKenzie, Suwanee, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 359 days.

(21) Appl. No.: 12/259,309

(22) Filed: Oct. 28, 2008

(51) Int. Cl.
*G06Q 50/00* (2006.01)
(52) U.S. Cl. .............................................. 705/2; 705/3
(58) Field of Classification Search ................... 705/2, 3
See application file for complete search history.

(56) References Cited

U.S. PATENT DOCUMENTS

| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |

(Continued)

FOREIGN PATENT DOCUMENTS
CA 2482370 3/2006
(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Gerald J. O'Connor
*Assistant Examiner* — Neha Patel
(74) *Attorney, Agent, or Firm* — Sutherland Asbill & Brannan LLP

(57) ABSTRACT

Systems and methods may be provided for prescription pre-fill processing services, which may include receiving a pre-fill prescription claim request from a pharmacy computer; delivering the pre-fill prescription claim request to a claims processor; and receiving a first approved response from the claims processor, where the first approved response includes first financial coverage information. The systems and methods may also include delivering the first approved response to the pharmacy computer, where a prescription order of the drug or product is prepared for pickup by a customer, where the prepared prescription order is labeled in accordance with the first financial coverage information; delivering a prescription claim reversal request to the claims processor for a second adjudication; and receiving, by switch provider in accordance with the second adjudication, a second approved response that indicates a reversal of the first claim request, where the prepared prescription order of the drug or product remains ready for pickup by the customer.

20 Claims, 10 Drawing Sheets

U.S. PATENT DOCUMENTS

| | | | |
|---|---|---|---|
| 7,155,397 | B2 | 12/2006 | Alexander et al. |
| 7,337,129 | B1 * | 2/2008 | Lowry et al. ............ 705/2 |
| 7,471,993 | B2 * | 12/2008 | Rosenblum ............ 700/237 |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0039599 | A1 | 2/2004 | Fralic |
| 2004/0073457 | A1 | 4/2004 | Kalies |
| 2004/0078234 | A1 | 4/2004 | Tallal, Jr. |
| 2004/0117323 | A1 | 6/2004 | Mindala |
| 2004/0148198 | A1 | 7/2004 | Kalies |
| 2004/0249745 | A1 | 12/2004 | Baaren |
| 2005/0015280 | A1 | 1/2005 | Gabel et al. |
| 2005/0060201 | A1 | 3/2005 | Connely et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0240473 | A1 | 10/2005 | Ayers |
| 2005/0261939 | A1 * | 11/2005 | Augspurger et al. ............ 705/2 |
| 2005/0288972 | A1 | 12/2005 | Marvin et al. |
| 2006/0020514 | A1 | 1/2006 | Yered |
| 2006/0026041 | A1 | 2/2006 | Ullman et al. |
| 2006/0149784 | A1 | 7/2006 | Tholl et al. |
| 2006/0184391 | A1 | 8/2006 | Barre et al. |
| 2006/0259363 | A1 | 11/2006 | Jhetam |
| 2007/0005402 | A1 | 1/2007 | Kennedy et al. |
| 2007/0050209 | A1 | 3/2007 | Yered |
| 2007/0136100 | A1 | 6/2007 | Daugherty et al. |
| 2007/0233525 | A1 | 10/2007 | Boyle |
| 2007/0233526 | A1 * | 10/2007 | Hoffman et al. ............ 705/4 |
| 2007/0239493 | A1 | 10/2007 | Sweetland et al. |

FOREIGN PATENT DOCUMENTS

| | | |
|---|---|---|
| WO | 1995003569 | 2/1995 |
| WO | 2000039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

* cited by examiner

SYSTEMS AND METHODS FOR PRESCRIPTION PRE-FILL PROCESSING SERVICES

FIELD OF THE INVENTION

Aspects of the invention relate generally to prescription pre-filling and more particularly, to systems and methods for prescription pre-fill processing services.

BACKGROUND OF THE INVENTION

Prescription filling is typically performed by a pharmacy after receiving a request from a customer having a valid prescription. However, a pharmacy can enhance the customer experience and increase customer loyalty while streamlining its own workflow process by being proactive in anticipating the prescription filling needs of the customer. Accordingly, there is a need in the industry for pre-fill processing services.

SUMMARY OF THE INVENTION

According to an example embodiment of the invention, there may be a computer-implemented method. The method may include receiving, by a switch provider, a pre-fill prescription claim request from a pharmacy computer, where the pre-fill prescription claim request may identify a prescribed drug or product for a customer; delivering, by the switch provider, the pre-fill prescription claim request to a claims processor for a first adjudication; receiving, by the switch provider in accordance with the first adjudication, a first approved response from the claims processor for the pre-fill prescription claim request, where the first approved response may include first financial coverage information; and delivering, by the switch provider, the first approved response to the pharmacy computer, where in accordance with the delivered first approved response, a prescription order of the drug or product is prepared for pickup by the customer, where the prepared prescription order is labeled in accordance with the first financial coverage information. The method may also include delivering, by the switch provider, a prescription claim reversal request to the claims processor for a second adjudication; and receiving, by switch provider in accordance with the second adjudication, a second approved response that indicates a reversal of the first claim request by the claims processor, where the prepared prescription order of the drug or product may remain ready for pickup by the customer for a period of time subsequent to receiving the second approved response.

According to another example embodiment of the invention, there may be a system. The system may include a memory that stores computer-executable instructions, and a processor configured to access the memory. The processor may be further configured to execute the computer-executable instructions to (i) receive a pre-fill prescription claim request from a pharmacy computer, where the pre-fill prescription claim request may identify a prescribed drug or product for a customer, (ii) deliver the pre-fill prescription claim request to a claims processor for a first adjudication, (iii) receive, in accordance with the first adjudication, a first approved response from the claims processor for the pre-fill prescription claim request, where the first approved response may include first financial coverage information, (iv) deliver the first approved response to the pharmacy computer, where in accordance with the delivered first approved response, a prescription order of the drug or product is prepared for pickup by the customer, wherein the prepared prescription order is labeled in accordance with the first financial coverage information, (v) deliver a prescription claim reversal request to the claims processor for a second adjudication, (vi) and receive, in accordance with the second adjudication, a second approved response that indicates a reversal of the first claim request by the claims processor, where the prepared prescription order of the drug or product may remain ready for pickup by the customer for a period of time subsequent to receiving the second approved response.

BRIEF DESCRIPTION OF THE DRAWINGS

Reference will now be made to the accompanying drawings, which are not necessarily drawn to scale, and wherein.

DETAILED DESCRIPTION

Figure 1:
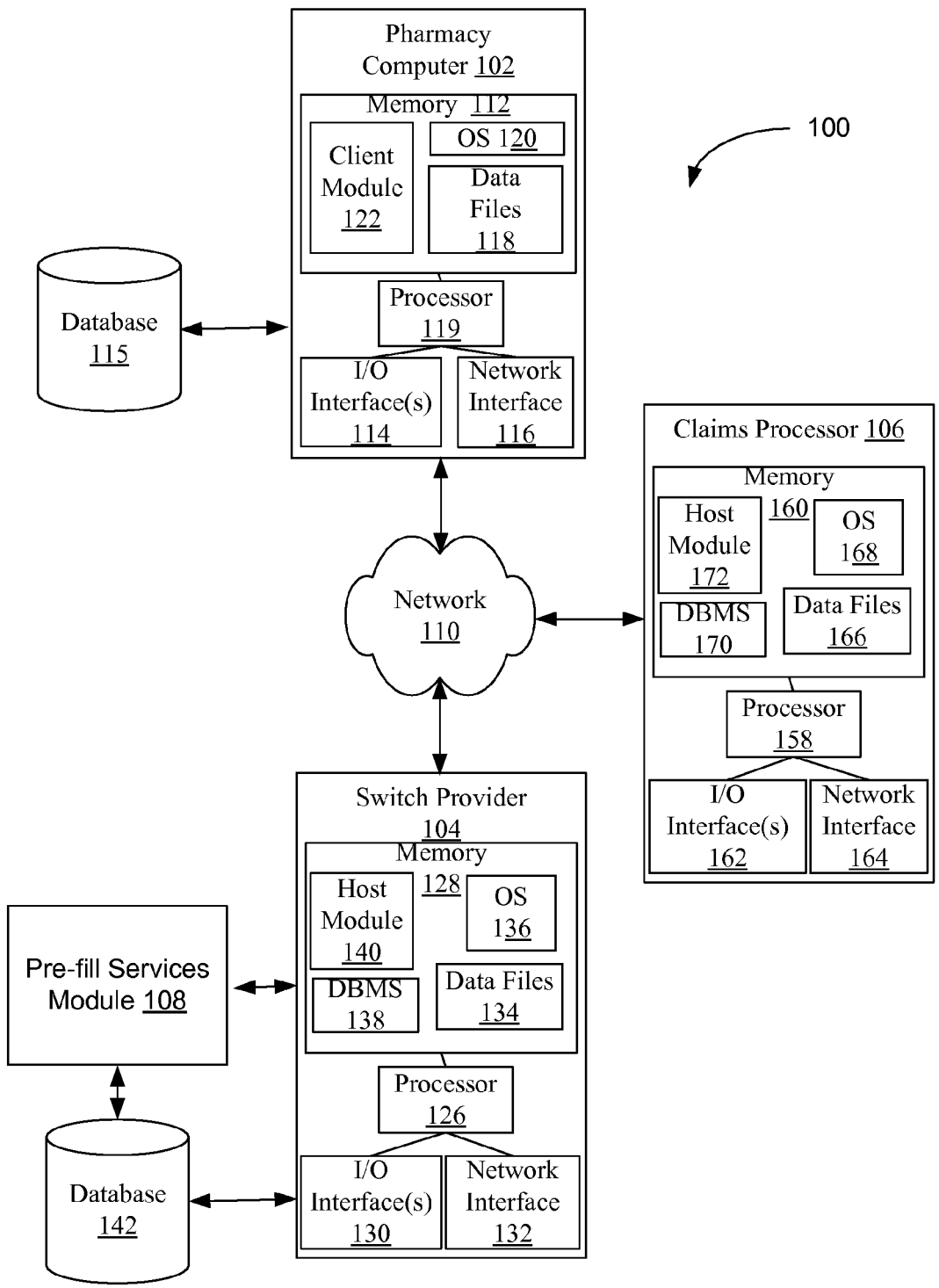
FIG. 1 illustrates an example system for supporting prescription pre-fill processing services, according to an example embodiment of the invention.

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may be described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, processor, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Example embodiments of the invention may be directed towards systems and methods for prescription pre-fill processing services. In accordance with such example prescription pre-fill processing services, a pharmacy may anticipate the filling or refilling needs of one or more of customers. The pharmacy may utilize a pre-fill prescription claim request and an offsetting reversal request, as described herein, in preparing a pre-filled prescription order for potential pickup. Accordingly, when the customer arrives at a pharmacy with a fill or refill request, the pre-filled prescription order may already be ready for pickup by the customer. Financial coverage discrepancies between the time the pre-filled prescription order was prepared and the time the customer arrives at the pharmacy with the fill or refill request may be resolved in a variety of ways, as described herein.

System Overview

FIG. 1 illustrates an example system 100 for supporting prescription pre-fill processing services, according to an example embodiment of the invention. As shown in FIG. 1, the system 100 may include a pharmacy computer 102, a switch provider 104, and a claims processor 106, which are each configured for accessing and reading associated computer-readable media having stored thereon data and/or computer-executable instructions for implementing the various methods of the invention. Generally, network devices and systems, including the one or more pharmacy computers 102, switch providers 104, and claims processors 106 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" may describe any form of memory or a propagated signal transmission medium. Propagated signals representing data and computer-executable instructions may be transferred between network devices and systems.

As shown in FIG. 1, the pharmacy computer 102, switch provider 104, and claims processor 106 may be in communication with each other via a network 110, which as described below can include one or more separate or shared private and public networks, including the Internet or a publicly switched telephone network. Each of these components—the pharmacy computer 102, switch provider 104, claims processor 106, and the network 110—will now be discussed in further detail.

First, the pharmacy computer 102 may be any processor-driven device, such as a personal computer, laptop computer, handheld computer, and the like. In addition to having a processor 119, the pharmacy computer 102 may further include a memory 112, input/output ("I/O") interface(s) 1134 and a network interface 116. The memory 112 may store data files 118 and various program modules, such as an operating system ("OS") 120 and a client module 122. The client module 122 may be computer-executable instructions or other software, including a dedicated program, for interacting with the switch provider 104 (and/or pre-fill services module 108) or the claims processor 106. For example, a user such as a pharmacist or other pharmacy employee may utilize the client module 122 in preparing and providing a prescription claim request or prescription claim reversal request to the switch provider 104 for delivery to the appropriate claims processor 106. The client module 122 may also be utilized to prepare and provide a pick-up message to the switch provider 104. Likewise, the client module 122 may further be utilized to retrieve or otherwise receive data, responses, or messages from the switch provider 104. The retrieved or received data, responses, messages, or other transaction information may be stored in a database 115. Similarly, transmitted data, requests, messages, or other transaction information may likewise be stored in the database 15.

Still referring to the pharmacy computer 102, the I/O interface(s) 114 may facilitate communication between the processor 119 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like.

The switch provider 104 may include any processor-driven device that is configured for receiving, processing, and fulfilling requests from the pharmacy computer 102 and/or claims processor 106 relating to prescription, pharmacy, benefits, and/or claim transactions or activities. The switch provider 104 may include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. The data files 134 may also store routing tables for determining the destination of communications received from the pharmacy computer 102, or claims processor 106. The host module 140 may receive, process, and respond to requests from the client module 122 of the pharmacy computer 102, and may further receive, process, and respond to requests from the host module 172 of the claims processor 106.

A pre-fill services module 108 may also be operative with the switch provider 104. The pre-fill services module 108 may include computer-executable instructions for identifying and responding to pre-fill transactions, including pick-up messages, pre-fill prescription claim requests, prescription claim reversal requests, and associated responses, according to an example embodiment of the invention. The pre-fill services module 108 may also record transaction information associated with the pre-fill transactions, perhaps in a database 142, according to an example embodiment of the invention. The pre-fill services module 108 may be implemented as part of the memory 128 of the switch provider 104. Alternatively, the pre-fill services module 108 may be implemented as part of a separate processor-based system that includes a memory for storing the computer-executable instructions, according to an example embodiment of the invention.

The claims processor 106 may include a processor 158, a memory 160, input/output ("I/O") interface(s) 162, and a network interface 164. The memory 160 may store data files 166 and various program modules, such as an operating system ("OS") 168, a database management system ("DBMS") 170, and a host module 172. The host module 172 may receive, process, and respond to requests from the client module 122 of pharmacy computer 102, and may further receive, process, and respond to requests from the host module 140 of the switch provider 104. According to an example embodiment of the invention, the claims processor 106 may be associated with benefits determination by a discount program, an insurance company, a pharmacy benefits manger (PBM), a government payor, or another third-party payor in accordance with an adjudication process. According to an alternative example embodiment of the invention, a claims processor 106 may also be implemented as part of a switch provider 104. By way of example, the claims processor 106 may be implemented as part of a switch provider 104 where non-funded cash transactions may be provided to the switch provider 104 to accommodate pre-fill processing services for cash customers.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between or among the pharmacy computer 102, the switch provider 104, and/or the claims processor 106. Due to network connectivity, various methodologies as described herein may be practiced in the context of distributed computing environments. It will also be appreciated that the network 110 may include a plurality of networks, each with devices such as gateways and routers for providing connectivity between or among networks 110. Instead of or in addition to a network 110, dedicated communication links may be used to connect the various devices in accordance with example embodiment invention. For example, the switch provider 104 may form the basis of network 110 that interconnects the pharmacy computer 102 with the claims processor 106.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Operational Overview

Figure 2A:
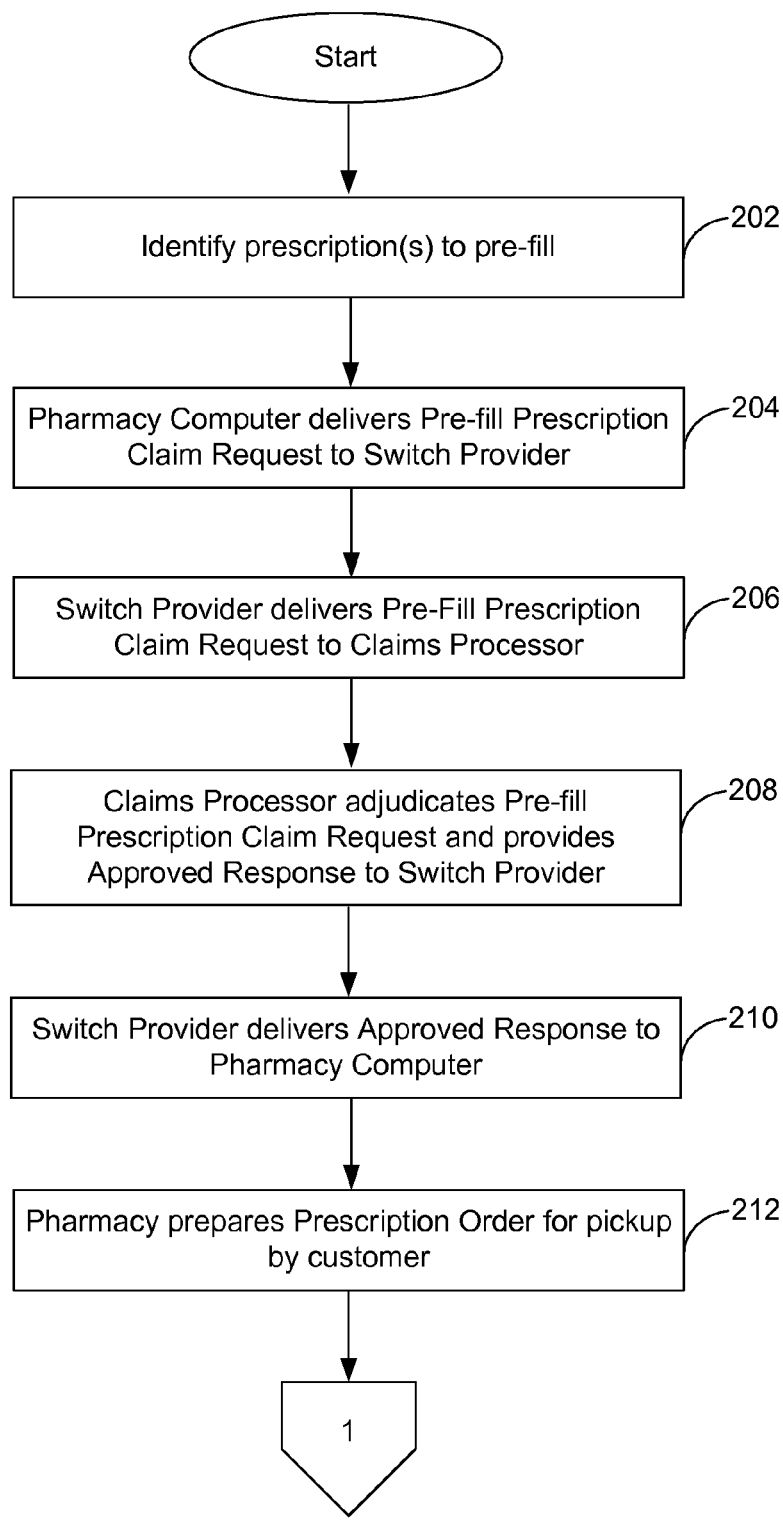
FIGS. 2A and 2B illustrate a flow diagram for providing pre-fill processing services in accordance with an example embodiment of the invention.
Figure 2B:
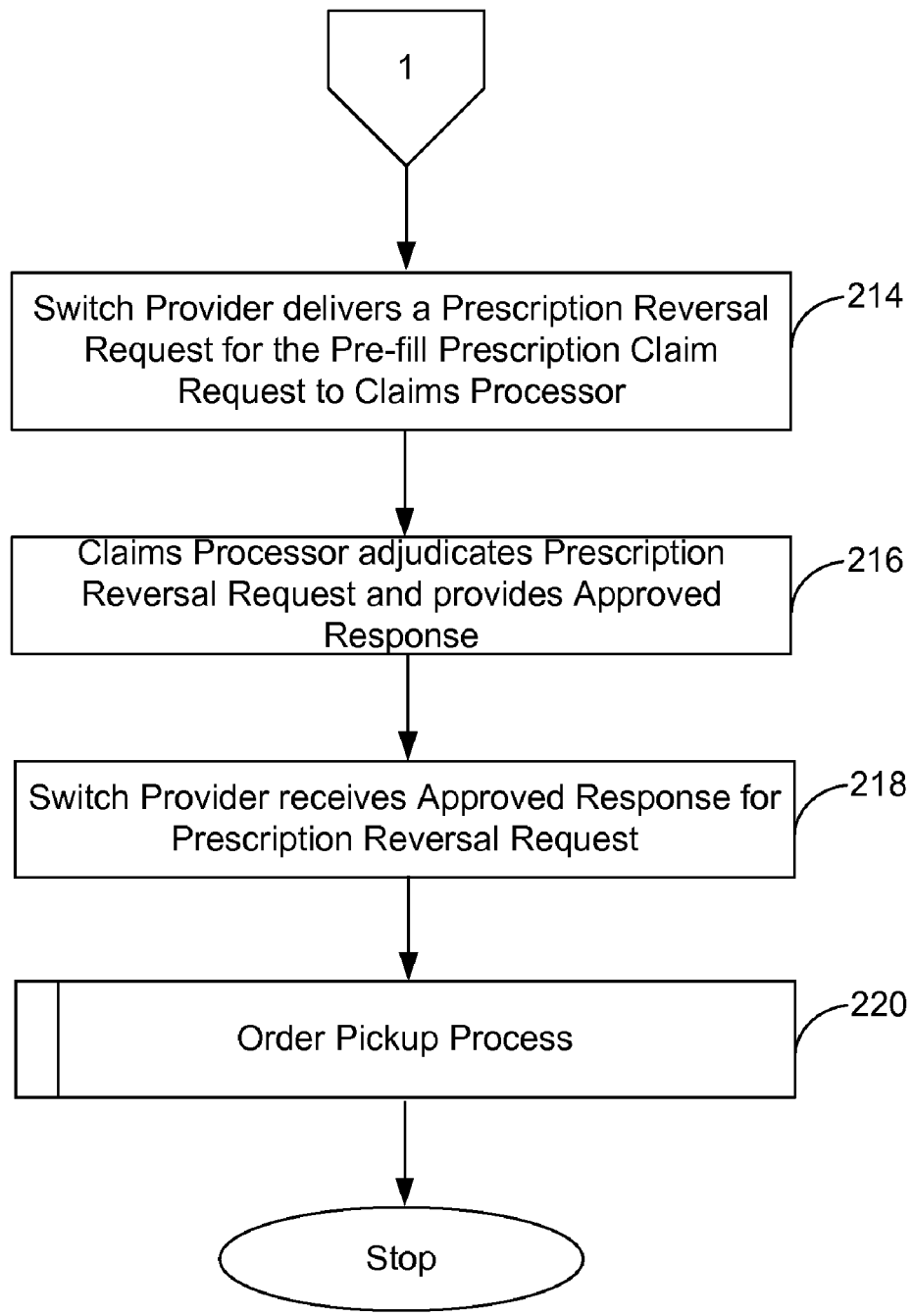

FIGS. 2A and 2B illustrate a flow diagram for providing pre-fill processing services in accordance with an example embodiment of the invention. The operation of the flow diagram of FIGS. 2A and 2B will be described in conjunction with the block diagram of FIG. 3A.

Referring now to block 202, a pharmacy (or pharmacist computer 102) or switch provider 104 may anticipate the fill or refill needs of a customer. Accordingly, the pharmacy or switch provider 104 may identify one or more prescriptions to pre-fill for one or more customers of a pharmacy. Indeed, these prescriptions to pre-fill may be identified prior to a pharmacy receiving an actual or specific fill or refill request from a customer.

According to an example embodiment of the invention, a pharmacy or switch provider 104 may identify one or more prescriptions to pre-fill in a variety of ways. In one example, a pharmacy or switch provider 104 may identify one or more prescribed drugs or products that have a high probability of being filled or refilled. As an example, these drugs or products may include maintenance medications, which are typically prescribed for long-term use. Accordingly, a pharmacy or switch provider 104 may identify customers that have filled or refilled a maintenance medication at particular pharmacy within a predetermined amount of time (e.g., within last 30 days, 90 days, etc.), and that may have one or more refills remaining.

According to another example embodiment of the invention, the identification of one or more prescriptions to pre-fill may be based upon enrollment by a customer. For example, a customer may enroll in a pre-fill pharmacy services program and indicate which medications he or she wishes for a pharmacy to track and pre-fill. In addition, the pharmacy or switch provider 104 may also utilize a payor inclusion or exclusion list to determine which customers are eligible for pre-fill pharmacy services. For example, customers receiving pharmacy benefits from a government payor may be excluded from receiving pre-fill pharmacy services, according to an example embodiment of the invention. On the other hand, customers associated with a particular pharmacy benefits manager (PBM) may be eligible for receiving pre-fill pharmacy services, according to an example embodiment of the invention.

It will be appreciated that additional or alternative business rules may be utilized for identifying one or more prescriptions to pre-fill for one or more customers of a pharmacy. For example, these business rules may be associated with determining which pharmacy a customer typically visits to fill a particular prescription or determining whether a customer has already refilled a prescription at a different pharmacy. Many variations will be available to those of ordinary skill in the art without departing from example embodiments of the invention.

In block 204, the pharmacy may have identified one or more prescriptions to pre-fill for one or more customers. For an identified prescription that is to be pre-filled, a pharmacy computer 102 may deliver a pre-fill prescription claim request 202 to the switch provider 104. According to an example embodiment of the invention, the pre-fill prescription claim request 302 may be in accordance with an NCPDP telecommunication standard, although other standards may be utilized as well. An example pre-fill prescription claim request 302 may include one or more of the following information:

Patient Information
  a. Name (e.g., Patient Last Name, Patient First Name, etc.)
  b. Gender
  c. Patent Address (e.g., Street Address, Zip Code, etc.)
  d. Patient Contact Information (e.g., Patient Telephone Number)
  e. Patient ID or other identifier
Insurance/Coverage Information
  a. Cardholder Name (e.g., Cardholder First Name, Cardholder Last Name)
  b. Cardholder ID or other identifier
Prescriber Information
  a. Primary Care Provider ID or other identifier (e.g., NPI code)

b. Primary Care Provider Name (e.g., Last Name, First Name)
c. Prescriber ID or other identifier (e.g., NPI code)
d. Prescriber Name (e.g., Last Name, First Name)
d. Prescriber Contact Information (e.g., Telephone Number)

Pharmacy Provider Information
a. Pharmacy ID (e.g., NPI code)

Claim Information
a. Drug or product information (e.g., National Drug Code (NDC)).
b. Date Prescription Written
c. Drug Quantity Dispensed
d. Number of Days Supply
e. Diagnosis/Condition
f. Pricing information for the drug or product
Date.

It will be appreciated that the pre-fill prescription claim request 302 may be a standard prescription claim request that has been designated as a pre-fill request. For example, an NCPDP prescription claim request may be designated as a pre-fill request by including a pre-fill identifier comprising one or more fields of the prescription claim request 302. For example, the pre-fill identifier may comprise one or more alpha-numeric codes or symbols in one or more fields according to an example embodiment of the invention. It will be also appreciated that while some example information has been illustrated for the example pre-fill prescription claim request 302, alternate or additional information may also be included without departing from example embodiments of the invention. For example, the pre-fill prescription claim request 302 may also include a Banking Identification Number (BIN) and a Processor Control Number (PCN) for identifying a claims processor 106 as a destination of the pre-fill prescription claim request 302. The pharmacy computer 102 may store, perhaps in a database 115, a copy of the pre-fill prescription claim request 302 that is delivered to the switch provider 104.

In block 206, the switch provider 104 may receive the pre-fill prescription claim request 302. The switch provider 104 may determine that the claim request 302 is associated with a pre-fill request and may provide a copy of the pre-fill prescription claim request 302 to the pre-fill services module 108 for storage in the database 142. The switch provider 104 may also determine the destination claims processor 106 based upon a BIN/PCN included with the pre-fill prescription claim request 302. The switch provider 104 may then route or otherwise deliver a copy of the pre-fill prescription claim request 302 to the destination claims processor 106 for coverage or benefits determination by a discount program, insurance company, PBM, government payor, or another third-party payor in accordance with an adjudication process. Where the claims processor 106 is part of the switch provider 104, the delivery of the pre-fill prescription claim request 302 may be an internal delivery. However, where the claims processor 106 is distinct from the switch provider, then the delivery of the pre-fill prescription claim request 302 may be an external delivery, perhaps via a network 110, according to an example embodiment of the invention.

In block 208, the claims processor 106 may adjudicate the pre-fill prescription claim request 302 and generate a claim response 304. The claim response 304 may include financial coverage information, including a covered amount (e.g., an insured amount) and a patient-responsible amount (e.g., a co-pay amount, coinsurance amount, deductible amount). Alternatively, the claim response 304 may indicate a denial of coverage for the pre-fill prescription claim request 302.

In block 210, the claims processor 106 may then deliver the claim response 304 to the switch provider 104. The switch provider 104 may determine that the claim response 304 is associated with a pre-fill request and provide a copy of the claim response 304 to the pre-fill services module 108 for storage in the database 142. The switch provider 104 may route or otherwise deliver the claim response 304 to the pharmacy computer 102, as illustrated in block 210. The pharmacy computer 102 may store, perhaps in a database 115, a copy of the claim response 304 that is received from the switch provider 104. If the claim response 304 does not indicate a denial, then the pharmacist or pharmacy employee may assemble the prescription order package for pickup by the customer. As part of the assembly process, the prescription order may be packaged with a prescription claim receipt in accordance with the financial coverage information in the received claim response 304.

In block 214, the pre-fill services module 108 may then access database 142 to determine one or more adjudicated pre-fill prescription claim requests that are to be reversed. In an example embodiment of the invention, the pre-fill services module 108 may delay the reversal of the adjudicated pre-fill prescription claim request for a period of time (e.g., several hours, 1 day, etc.) after the associated claim response 304 has been received and provided to the pharmacy computer 102. The delay in the reversal may be implemented to ensure that the patient-responsible amounts (e.g., deductible amounts) are calculated correctly for multiple pre-fill claim requests that may be submitted sequentially for a customer. Still referring to block 214, after passage of the delay, the switch provider 104 may receive a directive from the pre-fill services module 108 to reverse one or more adjudicated pre-fill prescription claim requests. The switch provider 104 may then route or otherwise deliver a prescription claim reversal request 306 to the claims processor.

In block 216, the claims processor 106 may adjudicate the prescription claim reversal request 306. Assuming the claims processor 106 is able to reverse or otherwise return the previously adjudicated and approved pre-fill prescription claim request 302, then the claims processor 106 may generate a reversal response 308 indicating that the requested claim reversal was successful. The claims processor 106 may provide or deliver the reversal response 308 to the switch provider 104.

In block 218, the switch provider 104 may receive the reversal response 308. The switch provider 104 may provide a copy of the reversal response 308 to the pre-fill services module 108. The pre-fill services module 108 may then update the database 142 to indicate that the corresponding prescription claim request 302 has been successfully reversed. In block 220, a order pickup process may be performed when a customer arrives at the pharmacy with a fill or refill request. Example order pickup processes will be discussed in conjunction with FIGS. 4-7, although other variations will also be available in accordance with example embodiments of the invention.

Figure 3A:
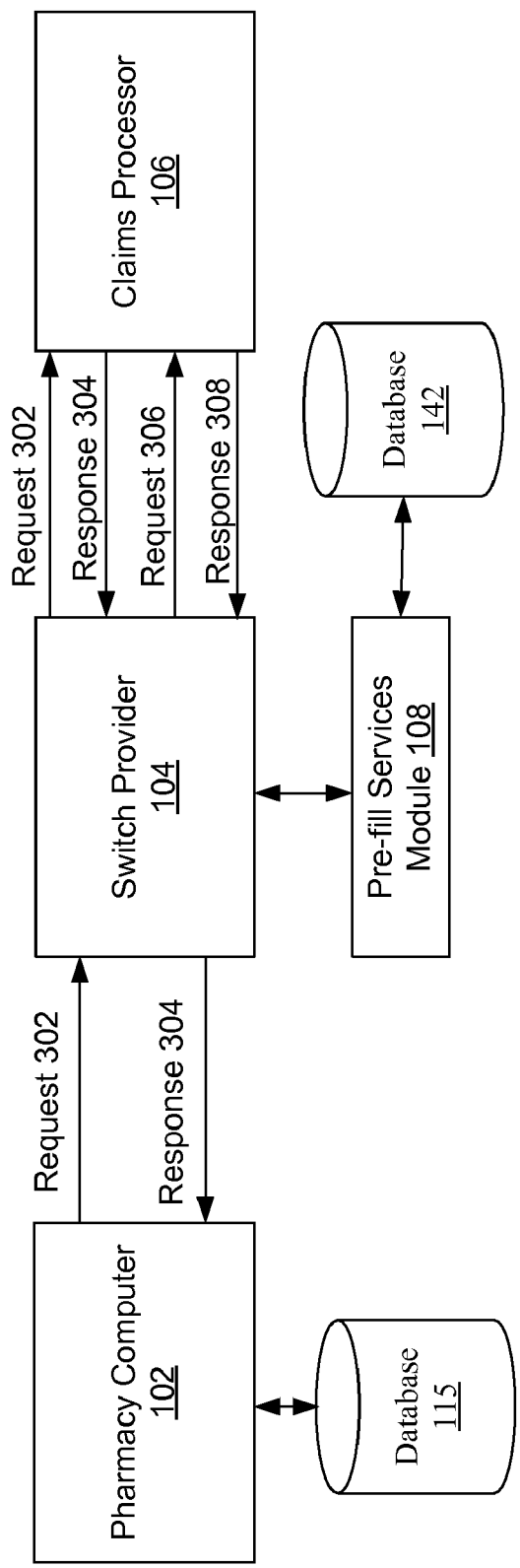
FIGS. 3A and 3B illustrates example block diagrams for providing pre-fill processing services in accordance with an example embodiment of the invention.

It will be appreciated that variations of FIGS. 2A-2B and 3A may be available in accordance with an example embodiment of the invention. For example, pre-fill requests for cash transaction customers may also be handled by providing a pre-fill cash transaction request from the pharmacy computer 102 to the switch provider 104. The pre-fill cash transaction request may include patient information, prescriber information, pharmacy provider information. In addition, the pre-fill transaction requests may specify a BIN/PCN that is specifically designated for handling pre-fill transactions for cash customers. By way of example, the BIN/PCN may specify an internal claims processor 106 that is provided as a component of the switch provider 104. The pre-fill services module 108 may then operate as described herein with the designated claims processor 106 and pharmacy computer 102 to provide pre-fill pharmacy services for cash customers.

Figure 3B:
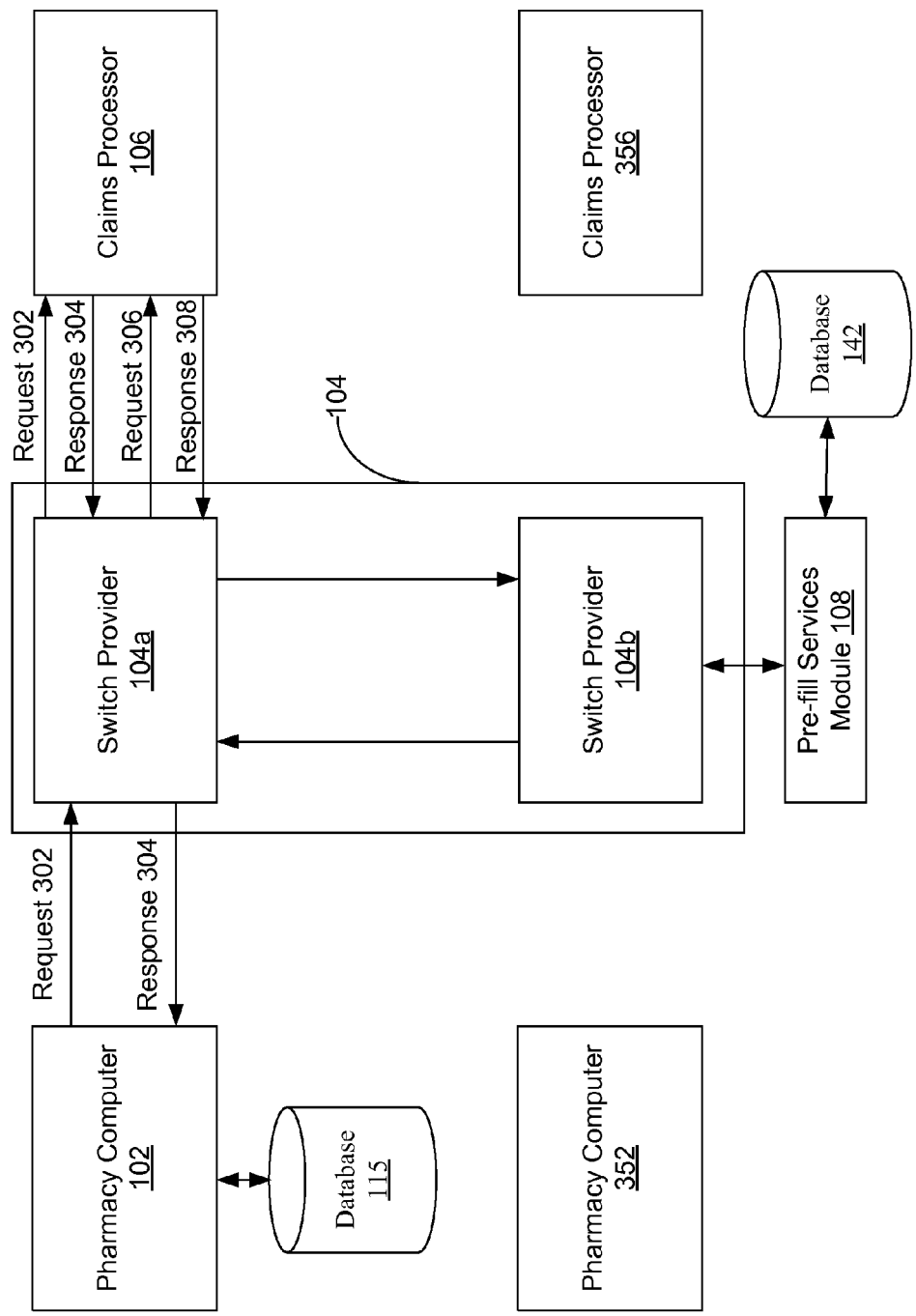

It will also be appreciated that yet other variations of FIGS. 2A-2B and 3A may be available in accordance with an example embodiment of the invention. For example, FIG. 3B illustrates a variation of the block diagram of FIG. 3A. As shown by FIG. 3B, the switch provider 104 may be comprised of two or more distinct switch providers 104a and 104b that are in communication with each other. Switch provider 104a may be operative with pharmacy computer 102 and claims processor 106 while switch provider 104b may be operative with pharmacy computer 352 and claims processor 358. However, switch provider 104b may have a data processing arrangement with switch provider 104a. Further, switch provider 104b may have direct access to one or more services, including those provided by the pre-fill services module 106. Under the data processing agreement, the switch provider 104a may be permitted to obtain services from the pre-fill services module 108 via switch provider 104b.

Figure 4:
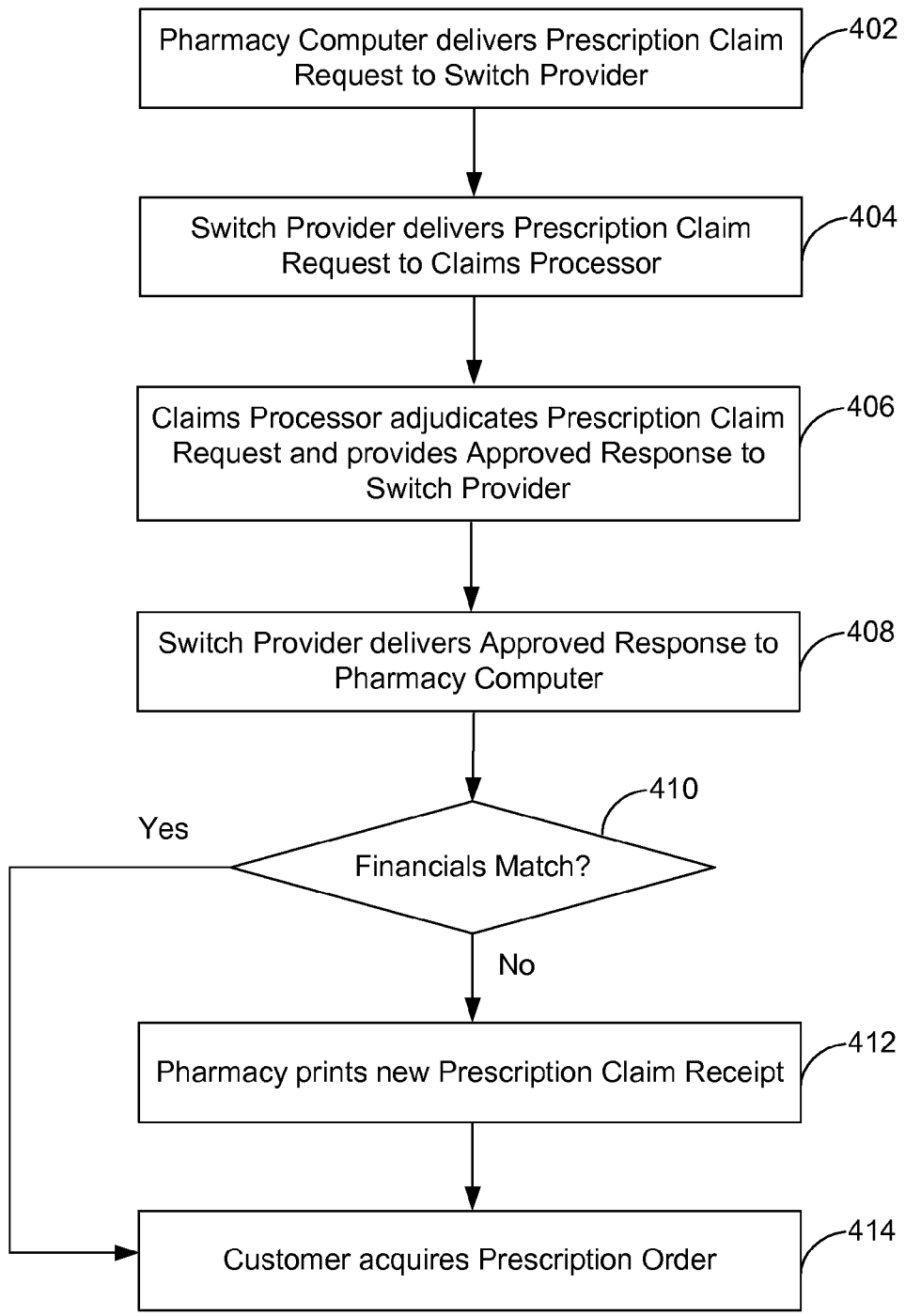
FIG. 4 illustrates an example flow diagram for an order pickup process, according to an example embodiment of the invention.

FIG. 4 illustrates an example flow diagram for an order pickup process, according to an example embodiment of the invention. It will be appreciated that the order pickup process illustrated in FIG. 4 may be utilized in accordance with block 220 of FIG. 2B, according to an example embodiment of the invention. The operation of the flow diagram of FIG. 4 will be discussed in conjunction with the block diagram of FIG. 5.

Figure 5:
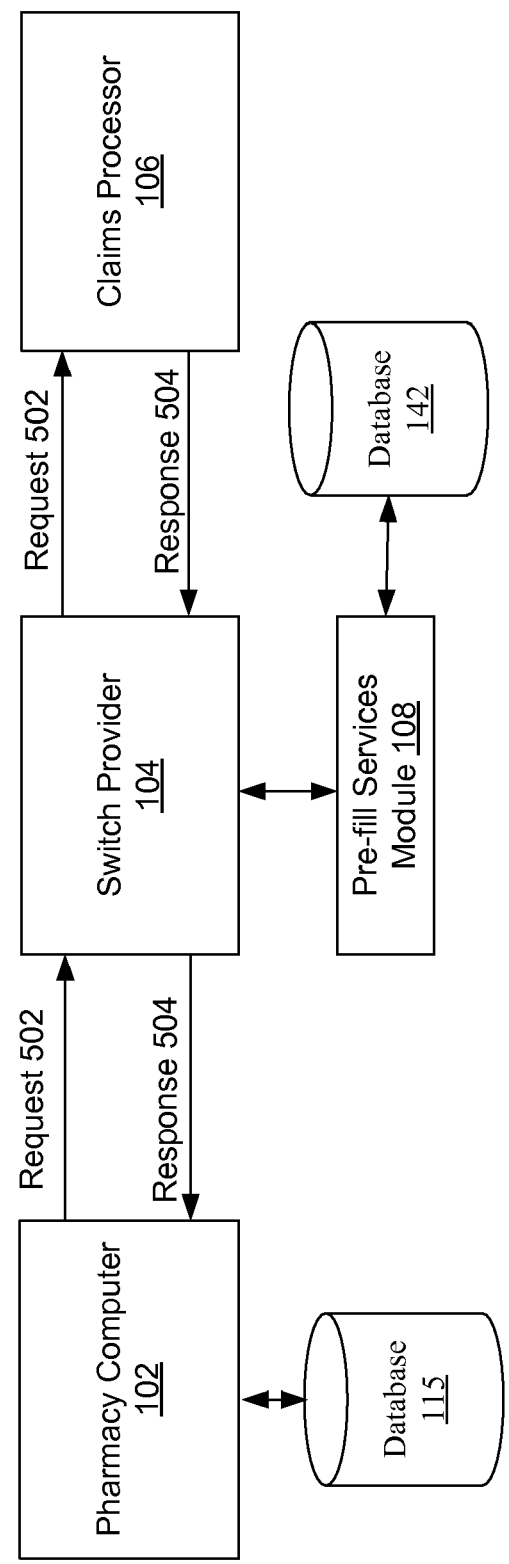
FIG. 5 illustrates an example block diagram for an order pickup process, according to an example embodiment of the invention.

Turning now to FIGS. 4 and 5, in block 402, the customer may arrive at a pharmacy requesting a prescription fill or refill. The pharmacist or pharmacy employee at the pharmacy may determine that the requested prescription fill or refill has previously been pre-filled, according to an example embodiment of the invention. The pharmacy computer 102 may then transmit or otherwise deliver a prescription claim request 502 to the switch provider 104. The prescription claim request 502 may include the following information:

Patient Information
  a. Name (e.g., Patient Last Name, Patient First Name, etc.)
  b. Gender
  c. Patent Address (e.g., Street Address, Zip Code, etc.)
  d. Patient Contact Information (e.g., Patient Telephone Number)
  e. Patient ID or other identifier
Insurance/Coverage Information
  a. Cardholder Name (e.g., Cardholder First Name, Cardholder Last Name)
  b. Cardholder ID or other identifier
Prescriber Information
  a. Primary Care Provider ID or other identifier (e.g., NPI code)
  b. Primary Care Provider Name (e.g., Last Name, First Name)
  c. Prescriber ID or other identifier (e.g., NPI code)
  d. Prescriber Name (e.g., Last Name, First Name)
  d. Prescriber Contact Information (e.g., Telephone Number)
Pharmacy Provider Information
  a. Pharmacy ID (e.g., NPI code)
Claim Information
  a. Drug or product information (e.g., National Drug Code (NDC)).
  b. Date Prescription Written
  c. Drug Quantity Dispensed
  d. Number of Days Supply
  e. Diagnosis/Condition
  f. Pricing information for the drug or product Date.

It will be appreciated that additional or alternative information may be included in the prescription claim request 502, including a BIN/PCN designating a particular claims processor 106 as a destination of the prescription claim request 502.

In block 404, the switch provider 104 may receive the prescription claim request 502. The switch provider 104 may then route or otherwise deliver a copy of prescription claim request 502 to the destination claims processor 106 for coverage or benefits determination by a discount program, insurance company, PBM, government payor, or another third-party payor in accordance with an adjudication process. In block 406, the claims processor 106 may adjudicate the pre-fill prescription claim request 502 and generate a claim response 504. The claim response 504 may include financial coverage information, including a covered amount (e.g., an insured amount) and a patient-responsible amount (e.g., a co-pay amount, coinsurance amount, deductible amount). Alternatively, the claim response 504 may indicate a denial of coverage for the prescription claim request 502.

In block 406, the claims processor 106 may then deliver the claim response 504 to the switch provider 104. In block 408, the switch provider 104 may route or otherwise deliver a copy of the claim response 504 to the pharmacy computer 102. In block 410, the pharmacy computer 102, or a pharmacist or pharmacy employee, may determine whether the current financial coverage information (e.g., patient-responsible amount) in the claim response 502 matches the prior financial coverage information associated with the previously adjudicated pre-fill claim transaction. It will be appreciated that the determination in block 410 may be a manual determination or an automated (e.g., computer-implemented) determination. For example, the pharmacy computer 102 may retrieve, from database 115, a copy of the claim response 304 associated with the pre-fill prescription claim request 302 to obtain the prior financial coverage information. Alternatively, the pharmacist or pharmacy employee may obtain the prescription claim receipt previously packaged with the prescription order. If the prior and current financial coverage information do not match in block 410, then processing may proceed to block 412, where a new prescription claim receipt may be printed using the current financial coverage information in accordance with the claim response 504. The patient may then be responsible for payment of the patient-responsible amount indicated by the new prescription claim receipt. In block 414, the customer may then acquire the prescription order from the pharmacy.

On the other hand, block 410 may result in a determination that the prior and current coverage information do indeed match. In this case, the prior prescription claim receipt that was previously packaged with the prescription order does not need to be replaced. The patient may then be responsible for payment of the patient-responsible amount indicated by the prior prescription claim receipt. In block 414, the customer may acquire the prescription order from the pharmacy.

Figure 6A:
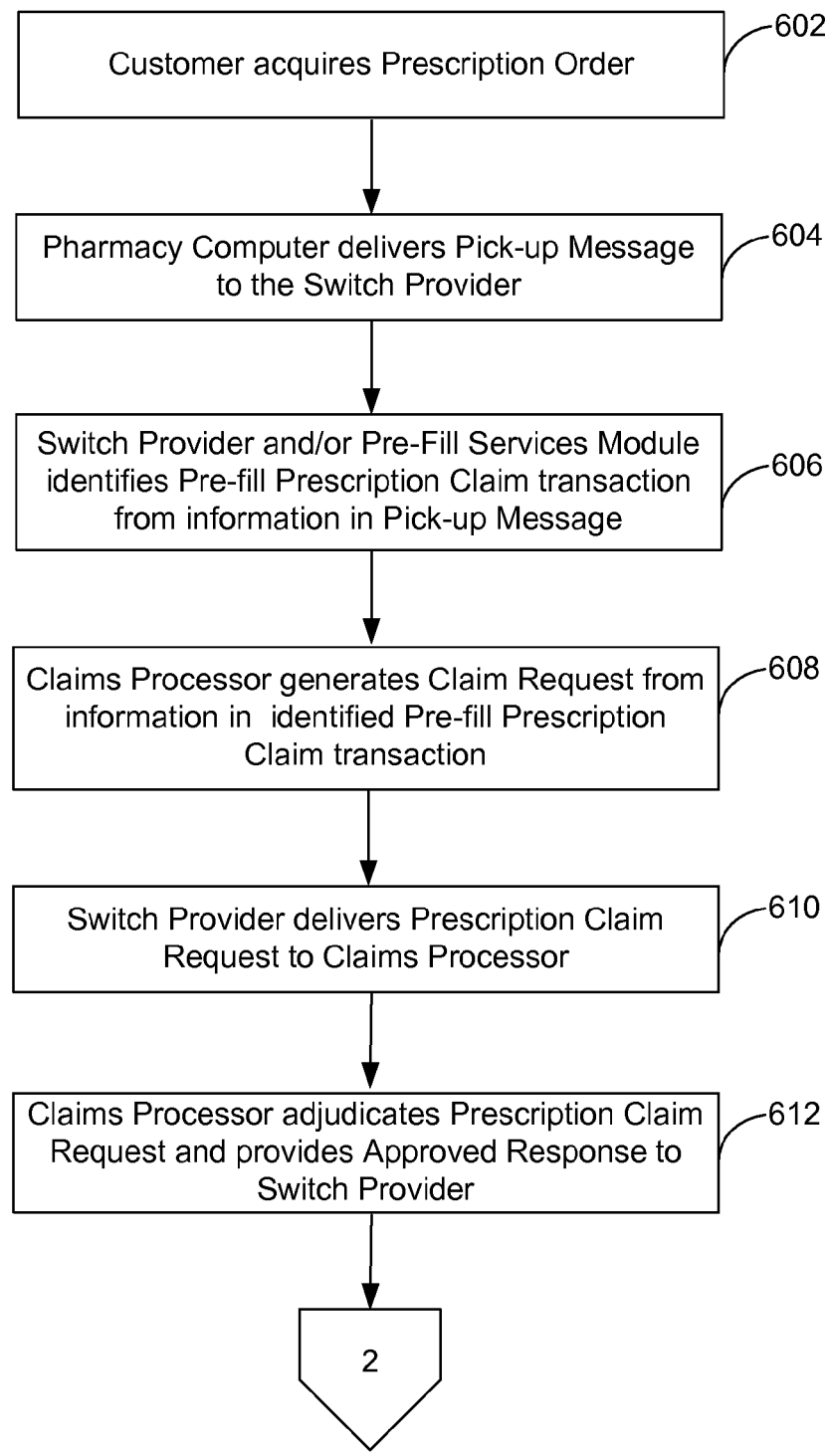
FIGS. 6A and 6B illustrate an example flow diagram for an alternative order pickup process, according to an example embodiment of the invention.
Figure 6B:
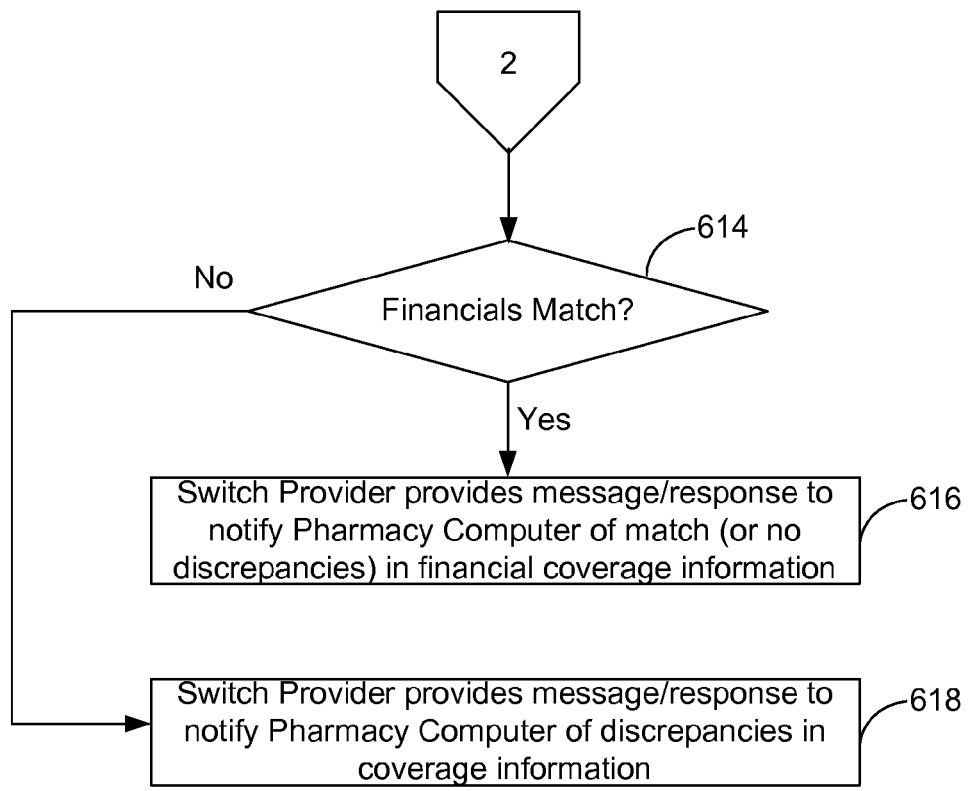

FIGS. 6A and 6B illustrate an example flow diagram for an alternative order pickup process, according to an example embodiment of the invention. It will be appreciated that the alternative order pickup process illustrated in FIGS. 6A and 6B may be utilized in accordance with block 220 of FIG. 2B, according to an example embodiment of the invention. The operation of the flow diagram of FIGS. 6A and 6B will be discussed in conjunction with the block diagram of FIG. 7.

In block 602, the customer may arrive at a pharmacy requesting a prescription fill or refill. The pharmacist or pharmacy employee at the pharmacy may determine that the requested prescription fill or refill has previously been pre-filled, according to an example embodiment of the invention. The pharmacy may then allow the customer to acquire the prescription order that was previously pre-filled. The customer may be responsible for payment of the patient-responsible amount indicated by the prescription claim receipt packaged with the prescription order. In block 604, the pharmacy computer 102 may deliver a pick-up message 702 to the switch provider 104. The pick-up message 702 may indicate that the previously packaged prescription order has been picked up by the customer. According to an example embodiment of the invention, the pick-up message 702 may include a pick-up indicator or other information for use in identifying a prior pre-fill claim transaction. For example, the pick-up message 702 may include a unique pick-up indicator that was included in the prior response 304 for identifying the pre-fill claim transaction. Alternatively, the pick-up message 702 may include information for use in identifying a prior pre-fill claim transaction, including Patient Information, Insurance/Coverage Information, Prescriber Information, Pharmacy Provider Information, Claim Information (including drug or product information), and/or a date associated with the prior pre-fill prescription claim transaction.

In block 606, the switch provider 104 may deliver the received pickup message 702 to the pre-fill services module 108. The pre-fill services module 108 may identify a corresponding pre-fill prescription claim transaction based upon the information in the pick-up message. For example, if the pick-up message 702 includes a unique pick-up indicator, then the pre-fill services module 108 may use the unique pick-up indicator to identify the matching pre-fill prescription claim transaction information (e.g., pre-fill prescription claim request/response and/or corresponding claim reversal request/response) stored in the database 142. Alternatively, the pre-fill services module 108 may identify the corresponding pre-fill prescription claim transaction information by matching or using one or more of Patient Information, Insurance/Coverage Information, Prescriber Information, Pharmacy Provider Information, Claim Information (including drug or product information), and/or a date of the prior pre-fill prescription claim transaction. It will be appreciated that there may be a variety of ways by which the pre-fill services module 108 may identify the corresponding pre-fill prescription claim transaction information, according to an example embodiment of the invention.

In block 608, the pre-fill services module 108 may provide the identified pre-fill prescription claim transaction information to the switch provider 104. The switch provider 104 may then generate a claim request 704 from the information in the identified pre-fill prescription claim transaction. According to an example embodiment of the invention, the claim request 704 may include the following information:

Patient Information
 a. Name (e.g., Patient Last Name, Patient First Name, etc.)
 b. Gender
 c. Patent Address (e.g., Street Address, Zip Code, etc.)
 d. Patient Contact Information (e.g., Patient Telephone Number)
 e. Patient ID or other identifier
Insurance/Coverage Information
 a. Cardholder Name (e.g., Cardholder First Name, Cardholder Last Name)
 b. Cardholder ID or other identifier
Prescriber Information
 a. Primary Care Provider ID or other identifier (e.g., NPI code)
 b. Primary Care Provider Name (e.g., Last Name, First Name)
 c. Prescriber ID or other identifier (e.g., NPI code)
 d. Prescriber Name (e.g., Last Name, First Name)
 d. Prescriber Contact Information (e.g., Telephone Number)
Pharmacy Provider Information
 a. Pharmacy ID (e.g., NPI code)
Claim Information
 a. Drug or product information (e.g., National Drug Code (NDC)).
 b. Date Prescription Written
 c. Drug Quantity Dispensed
 d. Number of Days Supply
 e. Diagnosis/Condition
 f. Pricing information for the drug or product
Date.

It will be appreciated that additional or alternative information may be included in the prescription claim request 704, including a BIN/PCN designating a particular claims processor 106 as a destination of the prescription claim request 704.

In block 610, the switch provider 104 may deliver the prescription claim request 704 to the destination claims processor 106 for coverage or benefits determination by a discount program, insurance company, PBM, government payor, or another third-party payor in accordance with an adjudication process. In block 612, the claims processor 106 may adjudicate the prescription claim request 704 and generate a claim response 706. The claim response 706 may include financial coverage information, including a covered amount (e.g., an insured amount) and a patient-responsible amount (e.g., a co-pay amount, coinsurance amount, deductible amount). Alternatively, the claim response 706 may indicate a denial of coverage for the pre-fill prescription claim request 704. The claim response 706 may be delivered from the claims processor 106 to the switch provider 104.

Block 614 may involve determining whether the current financial coverage information (e.g., patient-responsible amount) in the claim response 706 matches the prior financial coverage information associated with the previously adjudicated pre-fill claim transaction. It will be appreciated that the determination in block 614 may be a manual or automated (e.g., computer-implemented) process, and may be performed by the switch provider 104/pre-fill services module 108 (or alternatively, the pharmacy). For example, in block 614, the switch provider 104 may deliver a copy of the claim response 706 to the pre-fill services module 108. The pre-fill services module 108 may then determine whether the current financial coverage information (e.g., patient-responsible amount) in the claim response 706 matches the prior financial coverage information associated with the previously adjudicated pre-fill claim transaction. In particular, the pre-fill services module 108 may retrieve, from the database 142, a copy of the claim response 304 associated with the pre-fill prescription claim request 302 to obtain the prior financial coverage information. If the prior and current financial coverage information match in block 614, then the process may proceed to block 616. In block 616, the pre-fill services module 104 may direct or otherwise enable the switch provider 104 to optionally provide a response 708 to the pharmacy computer 102, where the response 708 includes a notification that there are no discrepancies in the prior and current financial coverage information.

On the other hand, if the prior and current financial coverage information do not match in block 614, then the process may proceed to block 618. In block 618, the pre-fill services module 104 may direct or otherwise enable the switch provider to provide a response 708 to the pharmacy computer 102, where the response 708 includes a notification that there no discrepancies in the prior and current financial coverage information. The pharmacy may be responsible for resolving any discrepancies in the prior and current financial coverage information.

Figure 7:
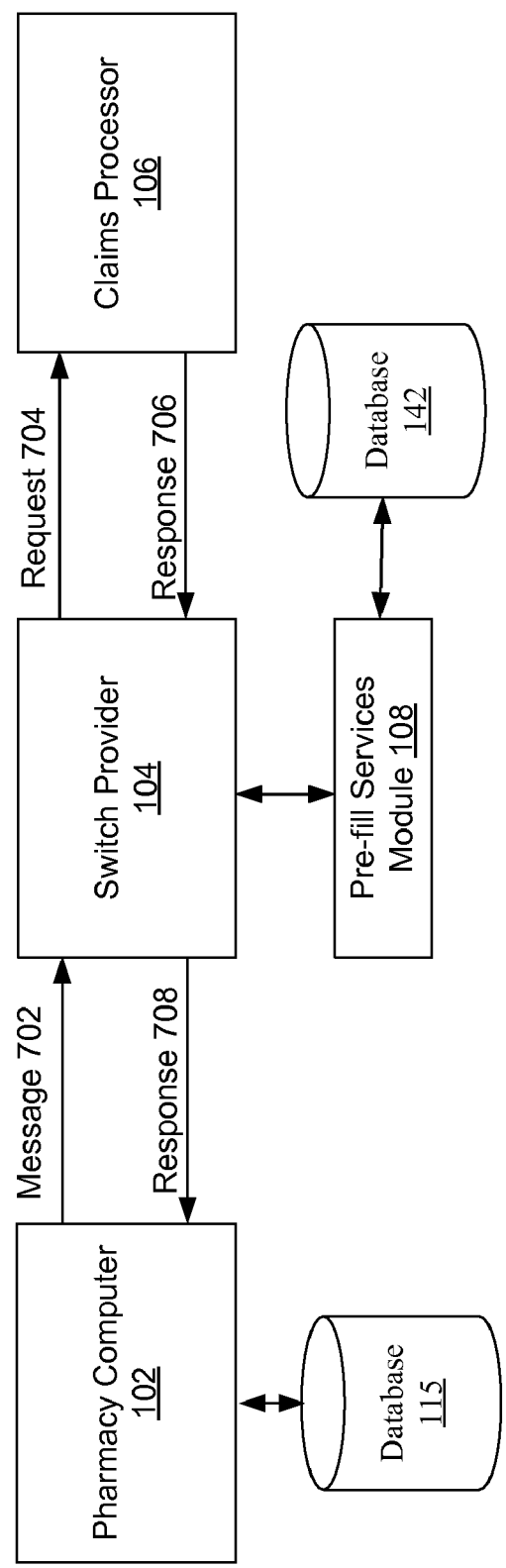
FIG. 7 illustrates an example block diagram for an alternative order pickup process, according to an example embodiment of the invention.

It will be appreciated that there are variations of FIGS. 6A-6B and FIG. 7 in accordance with example embodiments of the invention. According to one variation, the customer may acquire the prescription order subsequent to block 614 determining, either manually or electronically (e.g., computer-implemented), whether current financial coverage information (e.g., patient-responsible amount) in the claim response 706 matches the prior financial coverage information associated with the previously adjudicated pre-fill claim transaction. Accordingly, if there are no discrepancies, then the customer may be provided with the previously packaged prescription order having the prior prescription claim receipt. The patient may then be responsible for payment of the patient-responsible amount indicated by the prior prescription claim receipt. On the other hand, if there are discrepancies, then the response 708 to the pharmacy computer may include the information from the claim response 706 that includes the current financial coverage information. In this case, a new prescription claim receipt may be printed using the current financial coverage information included with the response 708. The patient may then be responsible for payment of the patient-responsible amount indicated by the new prescription claim receipt. Accordingly, in this alternative embodiment, financial coverage discrepancies may be resolved at the time the customer acquires the prescription.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method, comprising:
  receiving, by a switch provider computer, a pre-fill prescription claim request from a pharmacy computer, wherein the pre-fill prescription claim request identifies a prescribed drug or product for a customer, wherein the pre-fill prescription claim request is based upon anticipating a fill or refill need by the customer for the prescribed drug or product prior to receiving an actual request by the customer to fill or refill the prescribed drug or product;
  delivering, by the switch provider computer, the pre-fill prescription claim request to a claims processor for a first adjudication;
  receiving, by the switch provider computer in accordance with the first adjudication, a first approved response from the claims processor for the pre-fill prescription claim request, wherein the first approved response includes first financial coverage information;
  delivering, by the switch provider computer, the first approved response to the pharmacy computer, wherein in accordance with the delivered first approved response, a prescription order of the drug or product is prepared for pickup by the customer, wherein the prepared prescription order is labeled in accordance with the first financial coverage information;
  responsive to the first approved response, automatically delivering, by the switch provider computer, a prescription claim reversal request to the claims processor for a second adjudication; and
  receiving, by the switch provider computer in accordance with the second adjudication, a second approved response that indicates a reversal of the request by the claims processor, wherein the prepared prescription order of the drug or product remains ready for pickup by the customer for a period of time subsequent to receiving the second approved response.

2. The computer-implemented method of claim 1, further comprising:
  receiving, by the switch provider computer in accordance with a customer pickup of the prepared prescription order, a second prescription claim request from the pharmacy computer, wherein the second prescription claim request identifies the prescribed drug or product;
  delivering, by the switch provider computer, the second prescription claim request to the claims processor for a third adjudication;
  receiving, by the switch provider computer in accordance with the third adjudication, a third approved response from the claims processor, wherein the third approved response includes second financial coverage information; and
  delivering, by the switch provider computer, the third approved response to the pharmacy computer.

3. The computer-implemented method of claim 2, wherein the second financial coverage information is determined to be different than the first financial coverage information, and wherein the prepared prescription order is relabeled in accordance with the second financial coverage information prior to delivery to the customer.

4. The computer-implemented method of claim 3, wherein the pharmacy computer determines that the second financial coverage information is different from the first financial coverage information.

5. The computer-implemented method of claim 3, wherein the switch provider computer delivers a message indicating a difference between the second financial coverage information and the first financial coverage information to the pharmacy computer, wherein the prepared prescription order is relabeled in accordance with the delivered message.

6. The computer-implemented method of claim 1, further comprising:
  delivering, to the switch provider computer, a pick-up message from the pharmacy computer, wherein the pick-up message indicates that the prepared prescription order has been picked up by the customer;
  identifying, by the switch provider computer based upon information in the pick-up message, the previously received pre-fill prescription claim request;
  generating, by the switch provider computer based upon information in the pre-fill prescription claim request, a second prescription claim request;
  delivering, by the switch provider computer, the second prescription claim request to the claims processor for a third adjudication; and
  receiving, by the switch provider computer in accordance with the third adjudication, a third approved response from the claims processor for the second prescription claim request, wherein the third approved response includes second financial coverage information.

7. The computer-implemented method of claim 6, further comprising:
determining, by the switch provider computer, that the second financial coverage information matches the first financial coverage information; and
delivering, by the switch provider computer, a second message to the pharmacy computer, wherein the second message is indicative of the second financial coverage information matching the first financial coverage information.

8. The computer-implemented method of claim 6, wherein the second financial coverage information is determined to be different from the first financial coverage information.

9. The computer-implemented method of claim 8, wherein the switch provider computer delivers a second message to the pharmacy computer indicative of the second financial coverage information being different from the first financial coverage information.

10. The computer-implemented method of claim 1, wherein the pre-fill prescription claim request is received by the switch provider computer in accordance with a determination that the customer is likely to request a refill of the prescribed drug or product from the pharmacy within a second period of time.

11. A system, comprising:
at least one memory of at least one switch provider computer that stores computer-executable instructions; and
at least one computer processor of the at least one switch provider computer configured to access the at least one memory, wherein the at least one computer processor of the at least one switch provider computer is further configured to execute the computer-executable instructions to:
receive a pre-fill prescription claim request from a pharmacy computer, wherein the pre-fill prescription claim request identifies a prescribed drug or product for a customer, wherein the pre-fill prescription claim request is based upon anticipating a fill or refill need by the customer for the prescribed drug or product prior to receiving an actual request by the customer to fill or refill the prescribed drug or product,
deliver the pre-fill prescription claim request to a claims processor for a first adjudication;
receive, in accordance with the first adjudication, a first approved response from the claims processor for the pre-fill prescription claim request, wherein the first approved response includes first financial coverage information,
deliver the first approved response to the pharmacy computer, wherein in accordance with the delivered first approved response, a prescription order of the drug or product is prepared for pickup by the customer, wherein the prepared prescription order is labeled in accordance with the first financial coverage information,
responsive to the first approved response, automatically deliver a prescription claim reversal request to the claims processor for a second adjudication, and
receive, in accordance with the second adjudication, a second approved response that indicates a reversal of the pre-fill prescription claim request by the claims processor, wherein the prepared prescription order of the drug or product remains ready for pickup by the customer for a period of time subsequent to receiving the second approved response.

12. The system of claim 11, wherein the processor is further configured to execute the computer-executable instructions to:
receive, in accordance with a customer pickup of the prepared prescription order, a second prescription claim request from the pharmacy computer, wherein the second prescription claim request identifies the prescribed drug or product;
deliver the second prescription claim request to the claims processor for a third adjudication;
receive, in accordance with the third adjudication, a third approved response from the claims processor, wherein the third approved response includes second financial coverage information; and
deliver the third approved response to the pharmacy computer.

13. The system of claim 12, wherein the second financial coverage information is determined to be different than the first financial coverage information, and wherein the prepared prescription order is relabeled in accordance with the second financial coverage information prior to delivery to the customer.

14. The system of claim 13, wherein the pharmacy computer determines that the second financial coverage information is different from the first financial coverage information.

15. The system of claim 13, wherein the processor is further configured to execute the computer-executable instructions to:
deliver a message indicating a difference between the second financial coverage information and the first financial coverage information to the pharmacy computer, wherein the prepared prescription order is relabeled in accordance with the delivered message.

16. The system of claim 11, wherein the processor is further configured to execute the computer-executable instructions to:
deliver a pick-up message from the pharmacy computer, wherein the pick-up message indicates that the prepared prescription order has been picked up by the customer;
identify, based upon information in the pick-up message, the previously received pre-fill prescription claim request;
generate, based upon information in the pre-fill prescription claim request, a second prescription claim request;
deliver the second prescription claim request to the claims processor for a third adjudication; and
receive, in accordance with the third adjudication, a third approved response from the claims processor for the second prescription claim request, wherein the third approved response includes second financial coverage information.

17. The system of claim 16, wherein the processor is further configured to execute the computer-executable instructions to:
determine that the second financial coverage information matches the first financial coverage information; and
deliver a second message to the pharmacy computer, wherein the second message is indicative of the second financial coverage information matching the first financial coverage information.

18. The system of claim 16, wherein the second financial coverage information is determined to be different from the first financial coverage information.

19. The system of claim 18, wherein the processor is further configured to execute the computer-executable instructions to:
  deliver a second message to the pharmacy computer indicative of the second financial coverage information being different from the first financial coverage information.

20. The system of claim 11, wherein the pre-fill prescription claim request is received in accordance with a determination that the customer is likely to request a refill of the prescribed drug or product from the pharmacy within a second period of time.

* * * * *